United States Patent [19]

Lau

[11] Patent Number: 5,194,390
[45] Date of Patent: Mar. 16, 1993

[54] COMPOSITION FOR THE ASSAY OF ALBUMIN

[75] Inventor: Arthur L. Y. Lau, Sharon, Mass.

[73] Assignee: Miles Inc., Elkhart, Ind.

[21] Appl. No.: 215,275

[22] Filed: Jul. 5, 1988

[51] Int. Cl.$^5$ .......................................... G01N 33/68
[52] U.S. Cl. .................................................... 436/88
[58] Field of Search ............... 558/410, 388; 552/101,
552/106, 107, 108, 109, 111, 112, 113, 114, 115;
564/316, 321, 323, 324; 436/88

[56] References Cited

U.S. PATENT DOCUMENTS

| | | | |
|---|---|---|---|
| Re. 11,078 | 5/1890 | Hermann | 552/112 |
| Re. 21,467 | 12/1983 | Jones et al. | 552/107 |
| 412,615 | 10/1889 | Hermann | 552/112 |
| 476,413 | 6/1892 | Runkel | 552/107 |
| 501,104 | 7/1893 | Runkel | 552/106 X |
| 647,834 | 4/1900 | Hausdorfer et al. | 552/112 |
| 999,028 | 7/1911 | Hausdorbp et al. | 552/107 |
| 1,149,575 | 8/1915 | Gartner et al. | 552/109 |
| 2,116,827 | 5/1938 | Foldi | 552/112 X |
| 2,184,491 | 12/1939 | Foldi | 552/106 |
| 2,281,624 | 5/1942 | Schussler et al. | 552/115 |
| 2,458,328 | 1/1949 | Adams | 552/106 |
| 2,505,487 | 4/1950 | Green | 552/106 X |
| 2,598,660 | 6/1952 | Glickman | 552/106 X |
| 2,726,252 | 12/1955 | Balon et al. | 552/111 X |
| 2,828,341 | 3/1958 | Adams et al. | 564/321 |
| 2,828,342 | 3/1958 | Kranz et al. | 564/321 |
| 2,983,756 | 5/1961 | Kranz | 564/321 |
| 2,986,453 | 5/1961 | Collins | 536/88 X |
| 3,063,812 | 11/1962 | Collins | 436/88 |
| 3,095,277 | 6/1963 | Free et al. | 436/88 X |
| 3,121,612 | 2/1964 | Nicholls et al. | 436/88 |
| 3,122,420 | 2/1964 | Ballester et al. | 436/88 X |
| 3,222,388 | 12/1965 | Perelman | 558/410 X |
| 3,334,105 | 8/1967 | Szarvasi | 558/388 X |
| 3,347,941 | 10/1967 | Ballbster et al. | 552/101 X |
| 3,359,072 | 12/1967 | Rey et al. | 436/88 |
| 3,408,396 | 10/1968 | Suh et al. | 558/410 X |
| 3,429,900 | 2/1969 | Spatz et al. | 552/109 |
| 3,485,587 | 12/1969 | Keston | 436/88 X |
| 3,489,815 | 1/1970 | Kraus | 558/410 X |
| 3,522,280 | 7/1970 | Becker | 558/410 X |
| 3,533,749 | 10/1970 | Kleinman | 436/88 |
| 3,739,000 | 6/1973 | Lodolini et al. | 552/113 X |
| 3,810,933 | 5/1974 | Banucci | 558/410 X |
| 3,828,071 | 8/1974 | Kast et al. | 552/114 X |
| 3,873,272 | 3/1975 | Wakefield et al. | 436/88 |
| 3,884,637 | 5/1975 | Gindler | 436/88 |
| 4,013,416 | 3/1977 | Rittersdorf et al. | 436/88 X |
| 4,023,933 | 5/1977 | Bradford et al. | 436/88 X |
| 4,036,863 | 7/1977 | Karger et al. | 552/106 |
| 4,045,458 | 8/1977 | Kondo et al. | 552/106 |
| 4,076,728 | 2/1978 | Maulding | 552/106 X |
| 4,152,341 | 5/1979 | Jones et al. | 552/113 X |
| 4,318,859 | 3/1982 | Hermann | 552/113 X |
| 4,417,073 | 11/1983 | Ackermann et al. | 558/388 X |
| 4,528,136 | 7/1985 | Schmidt et al. | 552/106 |
| 4,613,465 | 9/1986 | Yamanishi | 552/112 |

FOREIGN PATENT DOCUMENTS

| | | | |
|---|---|---|---|
| 2456738 | 8/1976 | Fed. Rep. of Germany | 564/321 |
| 42-15026 | 8/1942 | Japan | 564/321 |
| 45-23833 | 8/1945 | Japan | 564/321 |
| 46-2973 | 1/1971 | Japan | 558/410 |
| 31641 | 3/1981 | Japan | |
| 62-204159 | 9/1987 | Japan | 436/88 |
| 63-261164 | 10/1988 | Japan | 436/88 |
| 27460 | 8/1930 | Netherlands | 552/101 |
| 856707 | 12/1960 | United Kingdom | 552/107 |
| 858019 | 1/1961 | United Kingdom | 552/107 |
| 1018563 | 1/1966 | United Kingdom | 436/88 |

OTHER PUBLICATIONS

Minch et al., J. Amer. Chem. Soc., vol. 97, pp. 3766 to 3772 (1975).
Schraufstaetter, Chemical Abstracts, vol. 60, 2862b (1964).
Sisedo et al., J. Org. Chem., vol. 19, pp. 1699 to 1703 (1954).
Sumrell et al., J. Amer. Chem. Soc., vol. 77, pp. 3805 to 3807 (1955).
Royball J. of Chromatography. 467 259 (1989).
Sanders, Clinica Chimica Acta 89, 421 (1978).
Ishidate et al., Ber. Deut. Chem. Gesell., vol. 74, pp. 163 to 173 (1941).
Kolmev, "Approved Lab. Technic", 5th Ed., p. 142 (1951).
Reichel, J. Soc. Dyers & Colourists, vol. 74, p. 708 (1958).

Primary Examiner—Robert Gerstl
Attorney, Agent, or Firm—Roger N. Coe

[57] ABSTRACT

A method and composition for the assay for albumin at an essentially neutral to an alkaline pH. The method utilizes indicator dyes that, when sufficiently buffered in a pH range of approximately 6 to approximately 8, allows the detection of albumin in urine or serum. The indicator dyes utilized in the method of the present invention have the general formula:

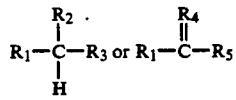

wherein $R_1$ and $R_2$ are substituted aromatic heterocyclic or carbocyclic moieties having one or more electron-withdrawing functionalities present on the aromatic ring; $R_3$ is a substituted aromatic heterocyclic or carbocyclic moiety having one or more electron-withdrawing functionalities present on the aromatic ring, or $R_3$ is a non-aromatic electron-withdrawing moiety; $R_4$ is a substituted quasi-aromatic quinone-like heterocyclic or carbocyclic moiety having one or more electron-withdrawing functionalities present on the quasi-aromatic quinone-like ring; and $R_5$ is a substituted aromatic heterocyclic or carbocyclic moiety having one or more electron-withdrawing functionalities, including at least one hydroxy functionality, present on the aromatic ring.

4 Claims, No Drawings

COMPOSITION FOR THE ASSAY OF ALBUMIN

FIELD OF THE INVENTION

The present invention relates to a method and composition for the assay for albumin at an essentially neutral to an alkaline pH by utilizing new indicator dyes. More particularly, the present invention is directed to determining the presence of albumin in urine or serum by utilizing an indicator dye that is capable of interacting with albumin and undergoing a color transition in the pH range of approximately 6 to approximately 8, and having the general formula:

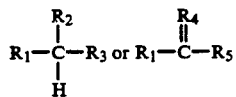

wherein $R_1$ and $R_2$ are substituted aromatic heterocyclic or carbocyclic moieties having one or more electron-withdrawing functionalities present on the aromatic ring; $R_3$ is a substituted aromatic heterocyclic or carbocyclic moiety having one or more electron-withdrawing functionalities present on the aromatic ring, or $R_3$ is a non-aromatic electron-withdrawing moiety; $R_4$ is a substituted quasi-aromatic quinone-like heterocyclic or carbocyclic moiety having one or more electron-withdrawing functionalities present on the quasiaromatic quinone-like ring; and $R_5$ is a substituted aromatic heterocyclic or carbocyclic moiety having one or more electron-withdrawing functionalities, including at least one hydroxy functionality, present on the aromatic ring.

BACKGROUND OF THE INVENTION AND PRIOR ART

Albumin is the most abundant plasma protein, generally constituting slightly over one-half of the total protein in mammalian plasma. In the human body, albumin has the important role of regulating the water balance between blood and tissues, and of functioning as a transport molecule for various compounds, such as bilirubin, fatty acids, cortisol, thyroxine and drugs such as sulfonamides and barbiturates, that are only slightly soluble in water. An albumin deficiency in individuals is indicated by an abnormal accumulation of serous fluid, or edema; and the albumin deficiency can restrict the transport of slightly water soluble materials throughout the body. Therefore, it is clinically important to determine whether an individual has a deficiency of serum albumin.

In addition, relatively high concentrations of albumin in the urine of an individual is indicative of a diseased condition. For example, the average normal concentration of protein in urine varies from about 2 mg/dL to about 8 mg/dL, with approximately one-third of the total urinary protein being serum albumin. However, in a majority of diseased states, urinary protein levels increase appreciably, such that albumin accounts for from about 60 percent to about 90 percent of the excreted protein. The presence of an abnormal increased amount of protein in the urine, known as proteinuria, is one of the most significant indicators of renal disease, and can be indicative of various other non-renal related diseases.

Therefore, in order to determine if an individual has an albumin deficiency and/or to determine if an individual excretes an excess amount of albumin, and in order to monitor the course of medical treatment to determine the effectiveness of the treatment, simple, accurate and inexpensive albumin detection assays have been developed. Furthermore, of the several different assay methods developed for the detection and/or measurement of albumin in urine and serum, the methods based on dye binding techniques have proven especially useful because dye binding methods are readily automated and provide reproducible and accurate results.

In general, dye binding techniques utilize pH indicator dyes that are capable of interacting with a protein, such as albumin, and that are capable of changing color upon interaction with a protein absent any change in pH. When a pH indicator dye interacts, or binds, to a protein, the apparent $pK_a$ (acid dissociation constant) of the indicator dye is altered and a color change occurs in the dye, producing the so-called "protein-error" phenomenon. In methods utilizing the dye binding technique, an appropriate buffer maintains the pH indicator dye at a constant pH to prevent a color change in the pH indicator dye due to a substantial shift in pH. Due to the "protein-error" phenomena, upon interaction with the protein, the pH indicator dye undergoes a color transition that is identical to the color change occurring because of a change in the pH. Examples of pH indicator dyes that are used in the wet phase chemistry assay of proteins capable of interacting or binding to protein and exhibiting "protein-error" color changes include methyl orange, bromocresol purple, bromophenol blue, and bromocresol green. Similarly, dry phase chemistry test strips utilize the pH indicator dyes tetrabromophenol blue and tetrachlorophenol-3,4,5,6-tetrabromosulfonephthalein.

Although pH indicator dyes have been used extensively in protein assays, several problems and disadvantages still exist in protein assay methods utilizing indicator dyes. For example, pH indicator dyes are useful only within narrow pH ranges. Outside the useful range of a dye, the dye either fails to change color upon interaction with the protein or the dye changes color prematurely. More importantly, and more difficult to overcome, albumin assays utilizing pH indicator dyes generally are conducted at relatively low pH (e.g., down to a pH of approximately 2 to 3; and normally at a pH of approximately 5 or below) in order to increase the interaction of the indicator dye with albumin and to permit a color transition to occur in the more commonly used dyes, such as bromocresol green and bromocresol purple, as a result of a pKa shift. However, since the acid-base transitions, and therefore the color transitions, of the more commonly used dyes occur at acidic pH values, non-specific interaction of these dyes with protein molecules other than albumin is increased. This potentially undesirable side effect occurs because at acidic pH values most proteins are cationic, or positively-charged, whereas the commonly used dye molecules can exist as negatively-charged anions. Therefore, interaction between the positively-charged cationic protein and negatively-charged anionic dye molecule is promoted. However, at higher pH values, most proteins become neutral or negatively-charged, and the non-specific ionic interactions with the indicator dye therefore are reduced.

Several simple semiquantitative tests and several complex quantitative tests are available for the determination of the total protein content in urine. The majority of these assay methods, with the notable exception of the simple colorimetric reagent test strip, require the precipitation of protein to make quantitative protein determinations. However, the colorimetric reagent test strip utilizes the previously discussed ability of proteins to interact with certain acid-base indicators and to alter the color of the indicator without a change in the pH. For example, when the indicator tetrabromophenol blue is buffered to maintain a constant pH of approximately 3, the indicator imparts a yellow color to solutions that do not contain protein; however, for solutions containing protein, the presence of protein causes the buffered dye to impart either a green color or a blue color to solution, depending upon the concentration of protein in the solution.

Some colorimetric test strips used in protein assays have a single test area consisting of a small square pad of absorbent paper impregnated with a buffered pH indicator dye, such as tetrabromophenol blue. Other colorimetric test strips are multideterminant reagent strips that include one test area for protein assay as described above, and further include several additional test areas on the same strip to permit the simultaneous assay of other urinary constituents. For both types of colorimetric test strips, the assay for protein in urine is performed simply by dipping the colorimetric test strip into a well mixed, uncentrifuged urine sample, then comparing the resulting color of the test area of the test strip to a standardized color chart provided on the colorimetric test strip bottle.

For test strips utilizing tetrabromophenol blue, buffered at pH 3, as the indicator dye, semiquantitative assays for protein can be performed and are reported as negative, trace, or one "plus" to four "plus". A negative reading, or yellow color, indicates that the urine contains no protein, as shown by the lack of color change of the indicator dye. A trace reading detects from about 5 to about 20 mg/dL of protein in the urine. The one "plus" to four "plus" readings, signified by a color change from green through increasingly dark shades of blue, are approximately equivalent to urine protein concentrations of 30, 100, 300, and 1000 mg/dL respectively, and serve as reliable indicators of increasingly severe proteinuria. It should be noted that a highly buffered, alkaline urine can give a false positive assay should the buffer system in the reagent test area be overcome and an actual shift in pH of the buffer occur.

The literature on the technology of dye binding to proteins is extensive and shows that protein sensitive dyes generally function at a fairly narrow pH range in the acidic region. Accordingly, Sanford, in U.S. Pat. No. 4,568,647, is the only known reference relating to a protein indicator dye that functions in the alkaline pH region.

Sanford discloses a method of assaying aqueous liquids for albumin, in a pH range of about 5 to about 11, utilizing a dye having a heterocyclic ring or a carbocyclic ring terminating each end of either a vinyl group or a conjugated polyene chain of up to seven carbon atoms. The dyes disclosed by Sanford preferentially bind to albumin over other proteins, and upon binding to albumin, the dyes exhibit a detectable shift in spectral absorption. The amount of albumin in the aqueous test sample can be quantitatively determined by measuring and correlating energy absorption of the aqueous test sample at the absorption maximum to the absorptions of solutions of known albumin concentration at the absorption maximum.

In contrast to the prior art and in contrast to the presently available commercial test strips, the indicator dyes useful in the method of the present invention can interact with albumin and as a result undergo a detectable color transition in a pH range that approximates the natural pH of urine and serum. Therefore, in accordance with an important feature of the present invention, extensive buffering of the indicator dye at an acidic pH is not required. As a result, the contamination of other assay pads, such as the urine pH assay pad, on a multiple pad test strip by the acidic components of the albumin assay pad is reduced or eliminated, thereby precluding the albumin assay from interfering with the simultaneous assay of other urine constituents.

Therefore, to avoid the potential contamination and resulting interferences associated with assays buffered in the acid pH region, it would be extremely advantageous to provide a method and composition for the assay of albumin in urine or serum at an essentially neutral to an alkaline pH. Likewise, it would be advantageous if the albumin assay method could be utilized in a dip-and-read format for the easy and economical, qualitative and/or semiquantitative determination of albumin in urine or serum.

Furthermore, any method for the assay of albumin in urine or serum must give accurate, trustworthy and reproducible results by utilizing a composition that undergoes a color transition as a result of an interaction with albumin, and not as a result of a competing chemical or physical interaction, such as preferential binding to proteins other than albumin. In addition, the method and composition for the albumin assay should be suitable for use both in wet assays and in dry reagent strips for the rapid, economical and accurate determination of albumin in urine or serum. Also, the method and composition utilized in the assay for albumin must not adversely affect or interfere with the other test reagent pads that are present on multiple test pad strips.

Prior to the present invention, no known composition or method of assaying urine or serum for albumin included a trisubstituted methane and/or a substituted phenolphthalein-type compound, that is capable of interacting with albumin and that is capable of undergoing a color transition at an essentially neutral to alkaline pH, as the indicator dye. Hence, in accordance with the method and composition of the present invention, new and unexpected results are achieved in the dry reagent strip assay and the wet assay of urine and serum for albumin by utilizing a trisubstituted methane indicator dye and/or a substituted phenolphthalein-type compound indicator dye buffered at an essentially neutral to an alkaline pH.

SUMMARY OF THE INVENTION

In brief, the present invention is directed to a composition and method of assaying urine or serum for albumin at an essentially neutral to an alkaline pH. It has been demonstrated that trisubstituted methane indicator dyes and/or substituted phenolphthalein-type indicator dyes, buffered in the pH range of about 6 to about 8, can interact with albumin and undergo a color transition to reveal the presence of albumin. By utilizing an indicator dye of the present invention in clinical test methods, the presence and/or semiquantitative concentration of albumin in a urine or serum sample can be determined by the intensity of the color change of the liquid test solution or the dry test pad.

Therefore, it is an object of the present invention to provide a simple, trustworthy, accurate and reproducible method of assaying urine or serum for albumin.

It is also an object of the present invention to provide a method of assaying urine or serum for albumin at an essentially neutral to an alkaline pH.

Another object of the present invention is to provide a method of assaying for albumin in urine and serum, at an essentially neutral to alkaline pH, that does not interfere with or provide erroneous results in simultaneous urine or serum assays for analytes other than albumin.

Another object of the present invention is to provide a dye composition that, when buffered in the pH range of from about 6 to about 8, can interact with albumin and undergo a detectable color change to establish the presence of albumin in urine or serum.

Another object of the present invention is to provide a dye composition that, when buffered in the pH range of from about 6 to about 8, can interact with albumin and undergo a visually and/or instrumentally differentiable color transition to allow the semiquantitative determination of the concentration of albumin in the urine or serum.

Another object of the present invention is to provide a trisubstituted methane dye compound and/or a substituted phenolphthalein-type dye compound that is capable of binding to albumin and undergoing a color change in the pH range of approximately 6 to approximately 8, and having the general structure

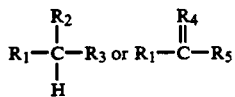

wherein $R_1$ and $R_2$ are substituted aromatic heterocyclic or carbocyclic moieties having one or more electron-withdrawing functionalities present on the aromatic ring; $R_3$ is a substituted aromatic heterocyclic or carbocyclic moiety having one or more electron-withdrawing functionalities present on the aromatic ring, or $R_3$ is a non-aromatic electron-withdrawing moiety; $R_4$ is a substituted quasi-aromatic quinone-like heterocyclic or carbocyclic moiety having one or more electron-withdrawing functionalities present on the quasiaromatic quinone-like ring; and $R_5$ is a substituted aromatic heterocyclic or carbocyclic moiety having one or more electron-withdrawing functionalities, including at least one hydroxy functionality, present on the aromatic ring.

Another object of the present invention is to provide a method of assaying for the presence and/or semiquantitative concentration of albumin in urine or serum utilizing a trisubstituted methane dye compound and/or a substituted phenolphthalein-type dye compound that is capable of interacting with albumin and undergoing a color change when buffered in the pH range of approximately 6 to approximately 8.

The above and other objects and advantages of the present invention will become apparent from the following detailed description of the invention.

DETAILED DESCRIPTION OF THE INVENTION

In accordance with the composition and method of the present invention, the qualitative and/or semiquantitative assay for albumin in urine or serum can be performed at an essentially neutral to alkaline pH by utilizing a trisubstituted methane indicator dye and/or a substituted phenolphthalein-type indicator dye. The indicator dyes of the present invention are capable of interacting with albumin and undergoing a detectable color transition within a pH range of about 6 to about 8 to show the presence and/or the approximate concentration of albumin in the urine or serum.

From the following detailed description of the invention, it will become apparent that, in addition to assaying urine, the method and composition of the present invention also can be used to determine the presence and semiquantitative concentration of albumin in blood plasma and serums; and more generally, the albumin content of many other albumin containing fluids as well. In accordance with another important feature of the present invention, the method and composition can be employed both in aqueous, liquid phase assays and in dry phase, test pad assays to determine the presence and/or approximate concentration of albumin in urine or serum.

Surprisingly and unexpectedly, a variety of trisubstituted methanes and substituted phenolphthalein-type compounds have demonstrated the ability to interact with albumin and undergo a detectable color change, at an essentially neutral to alkaline pH, to show the presence and/or approximate concentration of albumin in a urine or serum sample. The trisubstituted methanes and the substituted phenolphthalein-type compounds exhibiting the ability to interact with albumin and transform color have the general structures I and II, respectively:

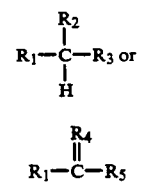

wherein $R_1$ and $R_2$ are substituted aromatic heterocyclic or carbocyclic moieties having one or more electron-withdrawing functionalities present on the aromatic ring; $R_3$ is a substituted aromatic heterocyclic or carbocyclic moiety having one or more electron-withdrawing functionalities present on the aromatic ring, or $R_3$ is a non-aromatic electron-withdrawing moiety; $R_4$ is a substituted quasi-aromatic quinone-like heterocyclic or carbocyclic moiety having one or more electron-withdrawing functionalities present on the quasiaromatic quinone-like ring; and $R_5$ is a substituted aromatic heterocyclic or carbocyclic moiety having one or more electron-withdrawing moieties, including at least one hydroxy functionality, present on the aromatic ring.

It has been found that the trisubstituted methanes of general structure I useful in the method of the present invention have at least two aromatic moieties covalently bound to the methane carbon atom, and each aromatic moiety has at least one electron-withdrawing functionality present on the aromatic ring. The third moiety of the trisubstituted methane also can be an aromatic moiety having electron-withdrawing functionalities present on the aromatic ring, or the third moiety can be a non-aromatic electron-withdrawing moiety. However, regardless of the aromaticity of the third moiety, the third moiety of the trisubstituted methane must be electron-withdrawing in nature.

It also has been found that the substituted phenolphthalein-type compounds of general formula II useful in the method of the present invention have two aromatic moieties covalently bound to the central carbon atom, and that each aromatic moiety has at least one electron-withdrawing functionality present on the aromatic ring. In addition, one of the two aromatic moieties bound to the central carbon atom must contain at least one electron-withdrawing hydroxy functionality. The third moiety of the substituted phenolphthalein-type compounds of general structure II is a quasi-aromatic quinone-like moiety having at least one electron withdrawing functionality present on the quinone-like ring.

As will be discussed more fully hereinafter, the aromatic rings, the electron-withdrawing functionalities present on the aromatic rings, and, if present, the non-aromatic electron-withdrawing moiety of the trisubstituted methanes of structural formula I serve to sufficiently increase the acidity of the trisubstituted methane such that the remaining hydrogen atom of the trisubstituted methane is easily removed at an essentially neutral to alkaline pH with resulting conversion of the trisubstituted methane to the anionic conjugate base of the trisubstituted methane. In addition to the inductive electron-withdrawing effect that increases the acidity of the trisubstituted methanes of structural formula I, the electron-withdrawing functionalities on the aromatic ring and, if present, any non-aromatic electron-withdrawing moiety help stabilize the anionic conjugate base of the trisubstituted methane by reducing the amount of negative charge on the methane carbon atom. Similarly, the electron-withdrawing functionalities on the aromatic and quasi-aromatic rings of the substituted phenolphthalein-type compounds of structural formula II serve to increase the acidity of the compound and also help to stabilize the anionic conjugate base of the phenolphthalein-type compound by reducing the amount of negative charge on the oxygen atom of the hydroxy functionality of moiety $R_5$.

The presence of at least two aromatic moieties on the trisubstituted methanes of structural formula I and the substituted phenolphthalein-type compound of structural formula II facilitates the stabilization of the negative charge by offering resonance structures that allow the negative charge of the anionic conjugate base to be distributed across the entire trisubstituted methane dye or substituted phenolphthalein-type dye molecule. Such resonance structures will be more fully described in the detailed description of the preferred embodiment of the present invention.

The unsubstituted aromatic heterocyclic or carbocyclic moieties bound to the central carbon atom of compounds having general structure I and II, and the unsubstituted quasi-aromatic quinone-like moiety bound to the central carbon atom of compounds having the general structure II, are not limited to any particular structure, as long as the moiety possesses sufficient aromatic character to provide resonance structures for the distribution of the negative charge of the anionic conjugate base throughout the aromatic or quasi-aromatic moiety. In accordance with the composition and method of the present invention, the aromatic moieties include carbocyclic aromatic ring systems, such as benzene, and carbocyclic aromatic fused ring systems, such as naphthalene. Furthermore, heterocyclic aromatic ring systems, including fused ring systems, wherein the heteroatom of the aromatic ring system includes one or more nitrogen, oxygen or sulfur atoms, or mixtures thereof, can be utilized in the method and composition of the present invention. Likewise, a fused aromatic ring system including both carbocyclic and heterocyclic aromatic rings can be used in accordance with the present invention.

To achieve the full advantage of the present invention, a benzene ring is utilized as the aromatic moiety. The benzene, or phenyl, ring is preferred because of its abundance, cost, and, especially, because of the ease of introducing a variety of electron-withdrawing functionalities onto the phenyl ring. The preferred carbocyclic and heterocyclic aromatic moieties that can be used in accordance with the present invention include benzene, pyrrole, furan, thiophene, pyridine, pyrazine, indole, quinoline, carbazole, purine, or mixtures thereof. Similarly, a quinone-like moiety as depicted in structural formula III is preferred as the quasi-aromatic quinone-like moiety $R_4$ found in general structure II.

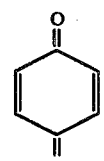

III

The above-mentioned aromatic and quasiaromatic carbocyclic and aromatic heterocyclic moieties are listed merely as examples of aromatic and quasi-aromatic moieties that can be used in accordance with the method and composition of the present invention, and these examples are not intended to limit the scope of the aromatic moieties that can be used according to the method of the present invention. It is envisioned that any aromatic or quasi-aromatic moiety, capable of having electron-withdrawing substituents present on the aromatic or quasi-aromatic ring, and possessing sufficient aromaticity to distribute the negative charge of an anionic conjugate base throughout the aromatic or quasi-aromatic moiety can be used in accordance with the present invention.

In accordance with another important feature of the present invention, each of the aromatic or quasi-aromatic moieties must include at least one electron-withdrawing functionality bound to aromatic ring. The electron-withdrawing functionality acts to further increase the acidity of the remaining methane hydrogen atom of compounds of general structure I and the acidity of the hydroxy hydrogen atom of compounds of general structure II, and to help further distribute the negative charge of the anionic conjugate base throughout the aromatic and quasi-aromatic moieties. The exact identity of the electron-withdrawing functionality is not particularly important, as long as the electron-withdrawing functionality imparts sufficient inductive electron-withdrawing effects to increase the acidity of the compounds of general structures I and II and to increase the stability of the anionic conjugate base. However, for compounds of general structure II, at least one of the two substituted aromatic moieties must have at least one hydroxy functionality present on the aromatic moieties.

The electron-withdrawing functionalities that can be bound to the heterocyclic or carbocyclic aromatic or quasi-aromatic moiety include ammonium ($-NH_3^+$), alkyl and/or aryl substituted ammonium ($-NH_2R^+$, $-NHR_2^+$, $-NR_3^+$), nitro ($-NO_2$), cyano ($-CN$), halo ($-Cl, -Br, -F, -I$), halo-substituted methyl ($-CH_2X$, $-CHX_2$, $-CX_3$, wherein X is chlorine, bromine, fluorine or iodine, or mixtures thereof), hydroxy (—OH), alkoxy or aryloxy (—OR), formyl (—CHO), carboxyl (—COOH), alkoxycarbonyl or aryloxycarbonyl (—COOR), carbamoyl (—CONH$_2$), alkyl and/or aryl-substituted carbamoyl (—CONHR, —CONR$_2$), aryl or alkyl carbonyl (—COR), 2-nitrovinyl(—CH=CHNO$_2$), alkyl or aryl sulfonyl (—SO$_2$R), sulfo (—SO$_3$H), phosphonium (—PH$_3^+$), alkyl and/or aryl-substituted phosphonium (—PH$_2$R$^+$, —PHR$_2^+$, —PR$_3^+$), sulfonium (—SH$_2^+$) or alkyl and/or aryl-substituted sulfonium (—SHR$^+$, —SR$_2^+$), or combinations thereof. For each of the above-mentioned electron-withdrawing functionalities, the alkyl group can contain from one to about twenty carbon atoms, and preferably from one to about ten carbon atoms. The aryl group can be any substituted or unsubstituted, heterocyclic or carbocyclic aromatic moiety.

The trisubstituted methanes of general structure I that serve as indicators for the detection of albumin in urine or serum also possess a third electron-withdrawing moiety in addition to the two substituted aromatic heterocyclic or carbocyclic moieties. The third electron-withdrawing moiety can be a substituted aromatic heterocyclic or carbocyclic moiety having one or more electron-withdrawing functionalities present on the aromatic ring identical to the aromatic moieties discussed above. It should be noted that if the trisubstituted methane contains three substituted aromatic moieties, it is not necessary that the three aromatic moieties be identical in respect either to the aromatic ring or to the type and/or number of electron-withdrawing functionalities present on the aromatic ring. In other words, the three substituted aromatic moieties can be identical; or two can be identical with the third having an independent structure; or all three aromatic moieties can be of independent structure. Analogously, a trisubstituted methane of general structure I and a phenolphthalein-like compound of general structure II that can be used in accordance with the method of the present invention and include only two substituted aromatic moieties, can have identical or structurally independent aromatic moieties. However, it has been found that because of considerations relating to the ease of trisubstituted methane dye or phenolphthalein-like dye synthesis, it often is desirable for the compounds of general structures I and II to have identical substituted aromatic moieties.

In accordance with another feature of the present invention, the third electron-withdrawing moiety of the trisubstituted methane of general structure I can be a non-aromatic electron-withdrawing moiety. It has been found that two substituted aromatic moieties provide sufficient delocalization and distribution of the negative charge of the anionic conjugate base to sufficiently stabilize the anion of the conjugate base. Therefore, the third electron-withdrawing moiety of the trisubstituted methane need only produce an electron-withdrawing inductive effect to increase the acidity of the trisubstituted methane of general structure I such that the remaining methane hydrogen of the trisubstituted methane can be removed in the pH range of about 6 to about 8.

In accordance with an important feature of the present invention, any electron-withdrawing moiety that increases the acidity of an alkyl hydrogen can be utilized as the third electron-withdrawing moiety of the trisubstituted methane of general structure I. However, it should be realized that the particular non-aromatic moiety selected for a particular trisubstituted methane is at least partially dependent upon the identity of the two aromatic moieties of the trisubstituted methane. For example, the selection of the particular non-aromatic third moiety of the trisubstituted methane depends upon considerations of ease of synthesis, chemical compatibility of the non-aromatic moiety with the aromatic moieties and/or the electron-withdrawing functionalities present on the aromatic moieties, stability of the dye, ability to undergo an acid-base reaction at an essentially neutral to an alkaline pH, and the ability to undergo a detectable color change and maintain the color change for a sufficient time at the desired pH.

Therefore, non-aromatic electron-withdrawing moieties that impart an acidity-increasing inductive effect upon the methane hydrogen, and that optionally may provide resonance structures to help stabilize the resulting anion of the conjugate base of the trisubstituted methane include nitro (—NO$_2$), cyano (—CN), alkoxy (—OR, wherein R is an alkyl group containing from one to about ten carbon atoms), aryloxy (—OR', wherein R' is a substituted or unsubstituted carbocyclic or heterocyclic aromatic ring system), carbonyl (—CO—Y, wherein Y is hydrogen, an alkyl group containing from one to about ten carbon atoms, an aryl or alkaryl group, an alkoxy group containing from one to about ten carbon atoms, an aryloxy or alkaryloxy group, amino, or an alkyl-, aryl- and/or alkaryl-substituted amino group wherein the alkyl group contains from one to about ten carbon atoms), halo (—Cl, —Br, —I, —F) or halo-substituted methyl (—CH$_2$X, —CHX$_2$, —CX$_3$, wherein X is chlorine, bromine, iodine, or fluorine), or combinations thereof. To achieve the full advantage of the present invention, it has been found that the nitro, the cyano and the alkoxy moieties are the non-aromatic electron-withdrawing moieties imparting the most desirable properties to a trisubstituted methane dye of general structure I used for the detection of albumin.

To show that a trisubstituted methane of general structure I can be utilized as an indicator dye to detect the presence of albumin in urine or serum according to the method of the present invention, the dye, cyanodi(p-nitrophenyl)methane, shown as structural formula IV, was prepared.

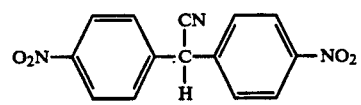

IV

As will be discussed more fully hereinafter, it has been demonstrated that the trisubstituted methane dye having structure IV, when buffered at a constant pH of about 7.5 to about 8.0, interacts with albumin and undergoes a color transition from colorless to blue. The three electron-withdrawing moieties of the trisubstituted methane of structure IV sufficiently increase the acidity of the remaining methane hydrogen, and sufficiently stabilize the resulting anion of the conjugate base of the trisubstituted methane such that the trisubstituted methane has a pKa in the range of 7.5 to 8.0. Therefore, the trisubstituted methane dye IV undergoes a color change, due to the protein-error phenomena, upon buffering at a constant pH of about 7.5 to about 8.0 and upon interacting with albumin. The stabilization of the anion of the conjugate base (V) is depicted by the following examples of possible resonance structures (VI through VIII). Likewise, several other degenerate resonance structures exist simultaneously with structures VI through VIII, and also act to stabilize the conjugate base V.

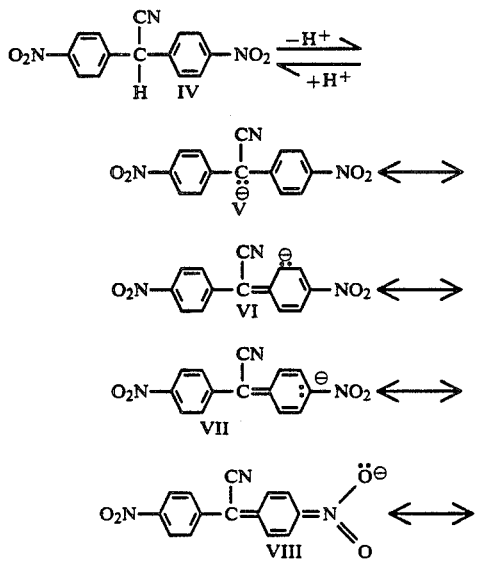

and several other degenerate resonance structures

Similarly, the substituted phenolphthalein-type dye illustrated as structural formula IX, the decyl ester of tetrabromophenolphthalein (TBDE), can be used in the method of the present invention to detect albumin in urine or serum. The substituted phenolphthalein-type dye IX includes two substituted aromatic moieties and one substituted quasi-aromatic quinone-like moiety, therefore differing slightly in structure from the trisubstituted methane dye III that includes two substituted aromatic moieties and a non-aromatic moiety. However, analogous to the trisubstituted methane dye IV, the substituted phenolphthalein-type dye IX, TBDE, when buffered at a constant pH of approximately 6.0 to 7.0, interacts with albumin and undergoes a color change from yellow to blue. The stabilization of the anion of the conjugate base of TBDE (IX) is depicted by the following examples of possible resonance structures X through XII.

hydrogen atom due to the "protein-error" phenomena to undergo a color transition. Therefore, the substituted phenolphthalein-type dyes of general structure II must include an aromatic moiety having at least one hydroxy functionality present on the aromatic ring.

The trisubstituted methane dye IV and the substituted phenolphthalein-type dye IX were prepared by synthetic methods well known to persons in the art, but according to a specific synthetic sequence. Furthermore, it is envisioned that other trisubstituted methane dyes and substituted phenolphthalein-type dyes useful in the method of the present invention can be prepared by similar synthetic methods and sequences, or may be commercially available.

The trisubstituted methane dyes and substituted phenolphthalein-type dyes described above are utilized as indicator dyes in a method to determine, at an essentially neutral to alkaline pH, the presence and/or the semiquantitative concentration of albumin in urine or serum. It has been demonstrated that the trisubstituted methane dyes and substituted phenolphthalein-type dyes of the present invention, upon buffering to a constant pH within a range of about 6 to about 8, can interact with albumin and undergo a visually and/or instrumentally detectable color change due to the "protein-error" phenomena. It has been found that by mixing the trisubstituted methane dye and/or the substituted phenolphthalein-type dye with a sufficient amount of a proper buffer, the dye cannot change color due to a pH shift, however, the resulting dye-buffer composition does change color upon contact and interaction with albumin to accurately indicate the presence and/or semi-quantitative concentration of albumin in the solution.

Further, it has been demonstrated that any of various known types of buffers can be used in the composition of the present invention. The function of the buffer is to maintain the composition at a substantially constant pH to produce the desired color change in the trisubstituted methane and/or substituted phenolphthalein-type dye because of the presence of albumin and to essentially eliminate color changes due to a variation in the pH of the albumin-containing test sample. As a result, the amount of buffer used depends upon the nature of the test solution. The quantity of buffer usually falls between about 200 millimolar and 500 millimolar, al-

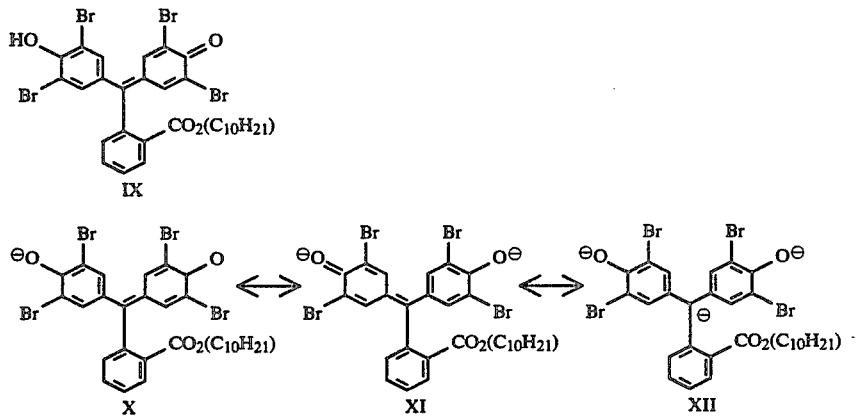

It should be noted that, unlike the trisubstituted methane dye IV that loses an acidic methane hydrogen atom, the substituted phenolphthalein-type dyes, of general structure II, and of structure IX, lose an acidic hydroxy though in particular cases it may be above or below this range. The nature of the buffer used will depend upon, and vary with, the trisubstituted methane dye and/or substituted phenolphthalein-type dye used. However, it generally has been found that for optimum results, the pH of the dye buffer composition should be maintained at a value only slightly below the pH range wherein the trisubstituted methane and/or substituted phenolphthalein-type dye undergoes a color transition. A method for determining the proper pH for the particular dye and the particular buffer used in the composition can be found in Keston, U.S. Pat. No. 3,485,587.

Although the use of a buffer in the present composition is preferred, it is not essential in all cases. For example, in special cases it may be desirable to add a buffer to the urine or serum test sample before the test sample contacts the trisubstituted methane dye and/or the substituted phenolphthalein-type dye. Also the test sample may already contain a buffer of the proper type and in the proper amount to maintain the system at a constant pH, or the trisubstituted methane dye and/or the substituted phenolphthalein-type dye may be insensitive to pH changes. In such cases, the trisubstituted methane indicator dye and/or the substituted phenolphthalein-type dye may be the sole active ingredient in the composition.

A color change of the trisubstituted methane dye and/or the substituted phenolphthalein-type dye demonstrates the presence of albumin in the urine or serum sample. In addition, the intensity and depth of the color transition can be used to determine the semiquantitative concentration of albumin in the urine or serum test sample by comparing the color produced by the test sample to colors produced by known concentrations of albumin in solution. It has been demonstrated that for some trisubstituted methane dyes and/or the substituted phenolphthalein-type dye the color change is readily detectable without the use of color-measuring instruments, such as spectrophotometers and colorimeters. However, such instruments can be helpful in differentiating the difference in color intensity between the test sample and a solution of known albumin concentration.

In accordance with an important feature of the present invention, the albumin assay is performed under the essentially neutral to alkaline pH conditions of about pH 6 to about pH 8. The ability to perform the albumin assay at a pH of about 6 to about 8 affords several advantages over the prior art albumin assays that require buffering in the acid pH region of 2 to about 5 in order to observe a color change in the dye. For example, by assaying at a pH that is close to the natural pH of urine and serum, extensive buffering to maintain a constant pH may not be required, and therefore, the effect of the buffer on the urine assay test pad, or on nearby test pads for other analytes, is minimal or non-existant.

Likewise, from a standpoint of clinical accuracy, an albumin assay performed at a pH level of 6 or above, decreases the non-specific interaction of the trisubstituted methane dye and/or substituted phenolphthalein-type dye molecule to proteins other than albumin. At the relatively high pH utilized in the method of the present invention, the competing proteins are present as a neutral or a negatively-charged molecule, not as a positively-charged molecule as exist at low pH values. Therefore, the possibility of non-specific interaction of a protein with a neutral trisubstituted methane dye such as IV, or its negatively-charged conjugate base V, or with a neutral substituted phenolphthalein-type dye such as IX or its negatively charged conjugate base X is reduced. As a result, the more specific interaction of the dye with the albumin decreases the interference presented by proteins of no interest, and increases the accuracy and reliability of the urine or serum albumin assay.

The assay for albumin in urine or serum conducted at an essentially neutral to alkaline pH affords other clinical benefits by eliminating or reducing the possibility of the albumin assay interfering with simultaneous assays for other urine or serum analytes. The interference between the albumin assay and other simultaneous analyte assays is most often observed in multiple pad test sticks. When using a multiple pad test stick, having several reagent-containing test pads closely positioned on a single stick, it is possible for the reagents present in one pad to runover and contaminate an adjacent and/or other nearby test pads, interfere with the analyte assay of the adjacent and/or nearby test pads, and therefore give erroneous and/or unreliable results.

For example, present day commercial multiple pad test sticks for urine include pH and albumin assays, plus several other analyte assays such as glucose, ketones, blood, specific gravity, nitrite, bilirubin, leukocyte esterase and urobilingen. Therefore, if the assay for albumin is a reagent pad having a pH indicator dye buffered in the acidic pH range of 2-3, any runover of reagents from the albumin assay pad to the pH assay pad would give erroneously low apparent pH values for urine, such as between 4 and 5. Such an error could be clinically significant because normal freshly-voided urine, from patients on a normal diet, has a pH of about 6. In general, the pH of urine can vary from about 4.6 to about 8.0, therefore accurate and trustworthy analyses of urine pH is a necessity for correct clinical determinations and resulting diagnosis.

Accordingly, an albumin assay that utilizes an indicator dye buffered at an essentially neutral to an alkaline pH, and therefore approximating the natural pH of urine, is less likely to contaminate a nearby pH assay pad on a multiple pad test stick and lead to inaccurate pH assay results. Overall, the accuracy of the various assays of the multiple pad test stick is improved, and the reliability of the assays, and therefore the confidence of the physician in the assays, also is improved. Additionally, because of the number of albumin assays being performed at home by the untrained patient, as opposed to trained physicians or technicians in the laboratory, it is imperative to have accurate and interference-free assay methods for albumin in urine.

To demonstrate the new and unexpected results afforded by utilizing a trisubstituted methane dye in the method of the present invention, cyanodi(p-nitrophenyl)methane (IV) was employed both in an aqueous, liquid phase assay for albumin, and in a dry phase, test pad assay for albumin. In the aqueous, liquid phase assay, the presence of albumin was demonstrated by adding one drop (approximately 50 uL (microliters)) of urine to a 2 ml (milliliter) aqueous solution including about $1 \times 10^{-2}$M (molar) of the trisubstituted methane dye IV, and buffered at a pH of about 7.5 with $1 \times 10^{-1}$M piperazine-N,N'-bis(2-hydroxypropane)sulfonic acid (POPSO). The color of the aqueous solution changed from colorless or a very pale blue to blue, therefore indicating the presence of albumin in the sample.

In general, in the aqueous, liquid phase assay for albumin, the trisubstituted methane dye and/or the substituted phenolphthalein-type dye is present in a sufficient amount to allow the visual and/or instrumental detection of a color change. It should be understood that the concentration of the trisubstituted methane indicator dye and/or substituted phenolphthalein-type indicator dye, the volume of the indicator dye/buffer solution and the volume of the urine can be varied considerably. The above example is intended to show a commonly used range of concentrations and volumes. However, a large excess amount of the trisubstituted methane dye and/or substituted phenolphthalein-type dye should be avoided such that non-specific interaction with proteins other than albumin is essentially precluded. Usually, a concentration of trisubstituted methane dye and/or substituted phenolphthalein-type dye in the range of about $5 \times 10^{-3}$M to about $5 \times 10^{-2}$M is sufficient to provide a visually and/or instrumentally detectable color change and to minimize assay interference through non-specific protein binding. It has been found, that to achieve the full advantage of the present invention, a trisubstituted methane dye and/or substituted phenolphthalein-type dye concentration in the range of about $8 \times 10^{-3}$M to about $2 \times 10^{-2}$M is employed. In accordance with the method of the present invention, it also has been found that in addition to the POPSO buffer used in the above example, the desired pH can be maintained at an essentially constant level by using any suitable buffer, such as N-2-hydroxyethyl-piperazine-N'-2-ethanesulfonic acid (HEPES), 3-N-(tris-hydroxymethyl)methylamino-2-hydroxypropanesulfonic acid (TAPSO), 2-([tris-(hydroxymethyl)methyl]amino)-ethanesulfonic acid (TES), phosphates, borates, or other buffers as are well known and practiced in the art.

Furthermore, in accordance with another important feature of the present invention, it is well within the skill of persons trained in the art to design a system for the semiquantitative assay of albumin in urine or serum by varying the relative amounts of aqueous solvent, trisubstituted methane dye and/or substituted phenolphthalein-type dye, buffer, and urine sample to provide visually and/or instrumentally detectable and differentiable color changes, such that a comparison to color standards derived from solutions of known albumin concentration is possible.

The dry phase, test pad assay for albumin utilizing a trisubstituted methane dye and/or substituted phenolphthalein-type dye is performed in accordance with methods well known in the prior art. In general, the albumin assay is performed by contacting an analyte detection device that includes the trisubstituted methane dye and/or substituted phenolphthalein-type dye with the urine or serum sample. The analyte detection device can be dipped into the urine or serum sample, or the urine or serum sample can be applied to the analyte detection device dropwise. A change in color of the analyte detection device demonstrates the presence of albumin, and, if so designed, the intensity and depth of the color change can be compared to a color chart to afford a semiquantitative measurement of the concentration of albumin in the urine or serum sample.

Typically, the analyte detection device is a reagent impregnated test strip, designed either as a single pad test strip (to assay only for a single analyte) or as a multiple pad test strip (to assay for several urine or serum analytes simultaneously). For either type of reagent impregnated test strip, the test strip includes a support strip, or handle, normally constructed from a hydrophobic plastic; and a reagent test pad, including a bibulous matrix, such as filter paper, sponge materials, hydrophilic inorganic powders, polymeric films or cellulose, impregnated with the chemical reagents required to perform the assay of interest. The handle is normally formed from materials such as cellulose acetate, polyethylene terephthalate, polycarbonate or polystyrene, and the bibulous matrix is most advantageously constructed from filter paper or polymeric films.

In accordance with the method of the present invention, to perform a dry phase, test stick assay for albumin, a dimethylformamide or ethanol solution, including $2 \times 10^{-2}$M of the cyanodi(p-nitrophenyl)methane dye (IV), first is prepared. A strip of filter paper then is saturated with the dimethylformamide or ethanol solution containing the dye. After removing the dimethylformamide or ethanol solvent by oven drying at about 50° C. for about 15 to about 30 minutes, the filter paper then is saturated with a 250 mM POPSO buffer at pH 7.5. After oven drying at about 50° C. for approximately 30 minutes, the reagent impregnated filter paper strip is cut to an appropriate size, such as a pad having dimensions from about 0.25 cm by about 0.5 cm to about 0.5 cm by about 1.0 cm. The reagent impregnated filter paper pad then is secured to the plastic handle with double sided adhesive. The test stick then was dipped into a fresh, uncentrifuged urine sample for a sufficient time to saturate the test pad with the sample. The test stick should not be immersed in the urine sample for longer than approximately 3 sec. to 5 sec. in order to avoid extraction of the buffer by the urine sample. After removing the test stick from the urine sample and waiting a predetermined time, such as 15 secs. to 60 secs., the test strip is examined for a response. A change in color of the test pad from essentially colorless to blue demonstrates the presence of albumin in the sample.

Analogous to the aqueous, liquid phase assay for albumin described above, it is well within the experimental techniques of those skilled in the art of preparing test devices to determine the proper balance between size of reagent pad, the strength of reagent impregnating solutions, the amount of test sample, and the method of introducing the test sample to the test stick, such as by pipetting rather than dipping, in order to design a semiquantitative assay for albumin utilizing the method and composition of the present invention.

In many cases simple visual observation of the test strip will provide the desired information. If more accurate information is required, a color chart bearing color spots corresponding to various known albumin concentrations, can be prepared for the particular trisubstituted methane indicator dye and/or substituted phenolphthalein-type dye used in the test strip. The color of the test strip then can be compared with the color spots on the chart to determine the albumin concentration of the test sample.

If a more accurate determination is required or if the trisubstituted methane is of such a character that it undergoes only a slight change in color, a spectrophotometer or colorimeter can be used to determine the color change. In addition, both the aqueous, liquid phase assay and the dry phase, reagent strip assay can be made semiquantitative by employing spectrophotometric or colorimetric techniques, as opposed to visual techniques, in order to more reliably and accurately measure the degree of color formation, and therefore more accurately measure the concentration of albumin in the test sample.

In accordance with an important feature of the present invention, accurate and reliable assays for albumin can be performed, at an essentially neutral to an alkaline pH, on urine and serum samples by utilizing a trisubstituted methane dye and/or a substituted phenolphthalein-type dye. By performing the albumin assay at the approximate natural pH of urine and serum, contamination of other simultaneous analyte assays by the reagents of the albumin assay are reduced or eliminated, therefore providing more accurate and reliable analyte assays.

Obviously, many modifications and variations of the invention as hereinbefore set forth can be made without departing from the spirit and scope thereof and therefore only such limitations should be imposed as are indicated by the appended claims.

I claim:

1. A composition capable of exhibiting a detectable color transition upon contact with an albumin-containing liquid test sample in the pH range of about 6 to about 8 to show the presence or concentration of albumin in the test sample, said composition comprising a dye having the formula:

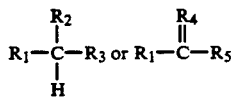

wherein $R_1$, $R_2$ and $R_3$ are aromatic moieties having one or more electron-withdrawing functionalities present on each $R_1$, $R_2$ and $R_3$ aromatic moiety; $R_4$ is a quasi-aromatic moiety having one or more electron-withdrawing functionalities present on the quasi-aromatic ring; and $R_5$ is an aromatic moiety having one or more electron-withdrawing functionalities, including at least one hydroxy functionality, present on the aromatic ring, wherein the aromatic moieties $R_1$, $R_2$, $R_3$ and $R_5$ are selected, independently, from the group consisting of benzene, naphthalene, pyrrole, furan, thiophene, pyridine, pyrazine, indole, quinoline, carbazole and purine, and wherien the electron-withdrawing functionalities present on the $R_1$, $R_2$, $R_3$, $R_4$ and $R_5$ moieties are selected, independently, from the group consisting of ammonium, aryl-substituted ammonium, nitro, cyano, halo, halo-substituted methyl, hydroxy, alkoxy, aryloxy, formyl, carboxyl, alkoxycarbonyl, aryloxycarbonyl, carbamoyl, alkyl-substituted carbamoyl, aryl-substituted carbamoyl, aryl carbonyl, alkyl carbonyl, 2-nitrovinyl, alkyl sulfonyl, aryl sulfonyl, sulfo, phosphonium, alkyl-substituted phosphonium, aryl-substituted phosphonium, sulfonium, alkyl-substituted sulfonium and aryl-substituted sulfonium, wherein an alkyl group contains from one to about twenty carbon atoms and an aryl group is an aromatic ring; and a buffer to maintain the composition at a pH in the range of about 6 to about 8.

2. The composition of claim 1 wherein the aromatic moiety is benzene.

3. The composition of claim 1 wherein the electron-withdrawing functionalities are selected from the group consisting of nitro, cyano, halo, halo-substituted methyl, hydroxy, alkoxy, aryloxy, formyl, alkoxycarbonyl, aryloxycarbonyl, alkyl carbonyl and aryl carbonyl.

4. The composition of claim 1 wherein the buffer is selected from the group consisting of piperazine-N-N'-bis(2-hydroxypropane)sulfonic acid, N-2-hydroxyethylpiperazine-N'-2-ethanesulfonic acid, 3-N-(tris-hydroxymethyl)methlamino-2-hydroxypropanesulfonic acid, 2-([tris-(hydroxymethyl)methyl]amino)ethanesulfonic acid, phosphates and borates.

* * * * *